(12) United States Patent
Odom et al.

(10) Patent No.: US 7,250,523 B2
(45) Date of Patent: Jul. 31, 2007

(54) IMIDO-TETHERED CARBENES OF MOLYBDENUM FOR RING-OPENING METATHESIS POLYMERIZATION AND RING-CLOSING METATHESIS

(75) Inventors: Aaron L. Odom, Lansing, MI (US); James T. Ciszewski, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 421 days.

(21) Appl. No.: 10/691,328

(22) Filed: Oct. 22, 2003

(65) Prior Publication Data

US 2005/0101475 A1 May 12, 2005

(51) Int. Cl.
*C07F 11/00* (2006.01)
*B01J 31/00* (2006.01)

(52) U.S. Cl. ............... 556/32; 556/57; 556/58; 548/402; 585/645; 502/152; 502/155; 502/162; 564/322; 564/441

(58) Field of Classification Search ........... 556/32, 556/57, 58; 548/402; 502/152, 155, 162; 564/322, 441
See application file for complete search history.

(56) References Cited

U.S. PATENT DOCUMENTS

| | | | |
|---|---|---|---|
| 4,727,215 A | 2/1988 | Schrock | |
| 5,142,073 A | 8/1992 | Schrock et al. | |
| 6,121,473 A | 9/2000 | Schrock et al. | |
| 6,197,715 B1 | 3/2001 | Bansleben et al. | |
| 6,313,332 B1 | 11/2001 | Grubbs et al. | |
| 6,316,555 B1 | 11/2001 | Schrock et al. | |
| 6,346,652 B1 | 2/2002 | Schrock et al. | |
| 6,410,664 B1 | 6/2002 | Bansleben et al. | |
| 6,414,097 B1 | 7/2002 | Grubbs et al. | |
| 6,482,908 B1 | 11/2002 | Grubbs et al. | |
| 6,486,279 B2 | 11/2002 | Lynn et al. | |
| 6,504,041 B2 | 1/2003 | Grubbs et al. | |
| 6,506,704 B1 | 1/2003 | Bansleben et al. | |
| 6,515,084 B2 | 2/2003 | Grubbs et al. | |
| 2001/0041778 A1 | 11/2001 | McConville et al. | |

OTHER PUBLICATIONS

Oskam et al., Journal of Organometallic Chemistry, vol. 459, No. 1-2, pp. 185-198 (1993).*
Gibson et al., J. Chem. Soc., Dalton Trans., vol. 2, pp. 161-165 (1999).*

(Continued)

*Primary Examiner*—Porfirio Nazario-Gonzalez
(74) *Attorney, Agent, or Firm*—Ian C. McLeod

(57) ABSTRACT

Compounds and processes for catalytic ring-opening cyclooligomerization metathesis and ring-closing metathesis of olefins are described. The compound is a molybdenum or tungsten metal (M) complex which comprises an imido ligand (N—R) bound to the M to provide an M=N—R site, an M=C reaction site wherein the C of the M=C reaction site is tethered to the R of the imido ligand via a carbon or carbon and heteroatom (NOS) chain containing 1 to 12 carbon atoms to form a ring structure, and two to four ligands (R') bound to the M to provide two to four M-R' sites. In particular embodiments, the M-R' sites include each of the oxygens of a dialkoxide ligand or each of the nitrogens of an $\eta^1$-pyrrolyl ligand bound to the M.

46 Claims, 1 Drawing Sheet

OTHER PUBLICATIONS

Ciszewski et al., Synthesis and structure of an imido-tethered Schrock carbene of molybdenum, Dalton Trans., pp. 4226-4227, published on the web Sep. 25, 2003.*

Alexander et al., J. Am. Chem. Soc. 120: 4041-4042 (1998).

La et al., J. Am. Chem. Soc. 120: 9720-9721 (1998).

Weatherhead et al., J. Am. Chem. Soc. 122: 1828-1829 (2000).

Cefalo et al., J. Am. Chem. Soc. 123: 3139-3140 (2001).

Hultzsch et al., Organometallics 20: 4705-4712 (2001).

Hultzsch et al., Agnew. Chem. Int. Ed. 41: 589-593 (2002).

* cited by examiner

US 7,250,523 B2

IMIDO-TETHERED CARBENES OF MOLYBDENUM FOR RING-OPENING METATHESIS POLYMERIZATION AND RING-CLOSING METATHESIS

STATEMENT REGARDING FEDERALLY SPONSORED RESEARCH OR DEVELOPMENT

This invention was made in the course of work supported by an Office of Naval Research Grant No. N00014-01-0638. The U.S. Government has certain rights in the invention.

Reference to a "Computer Listing Appendix Submitted on a Compact Disc"

Not Applicable.

CROSS-REFERENCE TO RELATED APPLICATION

Not applicable.

BACKGROUND OF THE INVENTION (1) Field of the Invention

The present invention relates to compounds and processes for ring-opening cyclooligomerization metathesis and ring-closing metathesis of olefins. The compound is a molybdenum or tungsten metal (M) complex which comprises an imido ligand (N—R) bound to the M to provide an M=N—R site, an M=C reaction site wherein the C of the M=C reaction site is tethered to the R of the imido ligand via a substituted carbon or carbon and heteroatom chain containing 1 to 12 carbon atoms to form a ring structure, and two to four ligands (R') bound to the M to provide two to four M-R' sites. In particular embodiments, the M-R' sites include each of the oxygens of a dialkoxide ligand or each of the nitrogens of an $\eta^1$-pyrrolyl ligand are bound to the M.

(2) Description of Related Art

Olefin metathesis is a reaction which in the presence of various transition metal catalysts, including various metal carbenes, the groups around the double bonds of olefins, are exchanged. This exchange enables a variety of reactions: cross metathesis wherein groups between two acyclic olefins are exchanged, ring-closing metathesis in which a compound with two olefins is converted into a cyclic product, ring-opening metathesis wherein dienes are formed from cyclic and acyclic olefins, ring-opening metathesis polymerization wherein cyclic olefins are polymerized into linear polymers, and acyclic diene metathesis polymerization wherein acyclic dienes are polymerized into linear polymers.

Improvements in the metal-carbene catalysts has led to the widespread use of olefin metathesis in organic synthesis. These improved catalysts are of two types: molybdenum or tungsten carbene catalysts (Schrock's catalyst) and ruthenium carbene catalysts (Grubbs' catalyst).

Schrock's catalyst and metathesis reactions using the catalyst have been described in U.S. Pat. No. 4,727,215 to Schrock; U.S. Pat. No. 5,142,073 to Schrock et al.; U.S. Pat. No. 6,121,473 to Schrock et al.; U.S. Pat. No. 6,316,555 B1 to Schrock et al.; U.S. Pat. No. 6,346,652 B1 to Schrock et al.; and, in published U.S. Patent Application No. 2001/0041778 to McConville et al. Schrock's catalyst and metathesis reactions using the catalyst have also been described in, for example, Totland et al., Macromolec. 29: 6114-6125 (1996); Alexander et al., J. Am. Chem. Soc. 210: 4041-4042 (1998); La et al., J. Am. Chem. Soc. 120: 9720-9721 (1998); Weatherhead et al., J. Am. Chem. Soc. 122: 1828-1829 (2000); Jamieson et al., Organometallics 19: 925-930 (2000); Cefalo et al., J. Am. Chem. Soc. 123: 3139-3140 (2001); Hultzsch et al., Organometallics 20: 4705-4712 (2001); and, Hultzsch et al., Agnew. Chem. Int. Ed. 41: 589-593 (2002).

Grubbs' catalyst and metathesis reactions using the catalyst have been described in U.S. Pat. No. 6,197,715 B1 to Bansleben et al.; U.S. Pat. No. 6,313,332 B1 to Grubbs et al.; U.S. Pat. No. 6,410,664 B1 to Bansleben et al.; U.S. Pat. No. 6,414,097 B1 to Grubbs et al.; U.S. Pat. No. 6,482,908 B1 to Grubbs et al.; U.S. Pat. No. 6,486,279 B2 to Lynn et al.; U.S. Pat. No. 6,504,041 to Grubbs' et al.; U.S. Pat. No. 6,506,704 B1 to Bansleben et al.; and, U.S. Pat. No. 6,515,084 B2 to Grubbs et al.

For both of these catalysts, the carbene is untethered. Therefore, at the end of the reaction, a relatively unstable methylidene, $M=CH_2$, complex is produced which often undergoes rapid decomposition. As a consequence, these catalysts are not reusable. Therefore, reactions in which these catalysts are supported on a solid substrate are less economically viable for many commercial applications than if they were reusable.

In light of the above, to render olefin metathesis reactions more economically viable for commercial applications, there is a need for molybdenum or tungsten carbene catalysts which are reusable.

OBJECTS

Therefore, it is an object of the present invention to provide processes for ring-opening cyclooligomerization metathesis and ring-closing metathesis of olefins which are more economically viable for commercial applications.

It is a further object of the present invention to provide molybdenum or tungsten carbene catalysts for cyclooligomerization metathesis and ring-closing metathesis of olefins which are reusable.

These and other objects of the present invention will become increasingly apparent with reference to the following drawings and preferred embodiments.

SUMMARY OF THE INVENTION

The present invention provides compounds and processes for catalytic ring-opening cyclooligomerization metathesis and ring-closing metathesis of olefins are described. The compound is a molybdenum or tungsten metal (M) complex which comprises an imido ligand (N—R) bound to the M to provide an M=N—R site, an M=C reaction site wherein the C of the M=C reaction site is tethered to the R of the imido ligand via a substituted carbon or carbon and heteroatom chain (N,S,O) containing 1 to 12 carbon atoms to form a ring structure, and two to four ligands (R') bound to the M to provide two to four M-R' sites. In particular embodiments, the M-R' sites include each of the oxygens of a dialkoxide ligand or each of the nitrogens of an $\eta^1$-pyrrolyl ligand bound to the M.

The present invention provides a compound which comprises a metal (M) complex with an imido ligand (N—R) bound to the M to provide an M=N—R site, a carbon (C) bound to the M to provide an M=C reaction site, a substituted carbon or carbon and heteroatom chain (N,S,O) containing 1 to 12 carbon atoms which tethers the C of the M=C reaction site to the R of the M=N—R site, and two to four ligands (R') bound to the M to provide two to four M-R' sites; wherein the M is selected from the group consisting of molybdenum and tungsten; the R and R' are each independently selected from the group consisting of alkyl, heteroalkyl, substituted alkyl, aryl, heteroaryl, substituted aryl, cyclic, heterocyclic, and substituted cyclic; and, the R' can be interconnected.

In a further embodiment, the R' are interconnected and each M-R' bond is between the M and an oxygen of a dialkoxide ligand or a nitrogen of an $\eta^1$-pyrrolyl ligand, particularly an $\eta^1$-pyrrolyl ligand which is N,N-di(pyrrolyl-α-methyl)-N-methylamine (dpma). In a further still embodiment, the R' is 1,2-dimethoxyethane or 3,3'-di-tert-butyl-5,5',6,6'-tetramethyl-1,1'-biphenyl-2,2'-diol.

In a further embodiment, the M is molybdenum.

In a further embodiment, a substituted alkyl chain between the C of the M=C and the R of the M=N—R comprises an alkylene backbone of 1 to 8 carbon atoms. In a further still embodiment, the substituted alkyl chain between the C of the M=C and the R of the M=N—R is —C(CH$_3$)$_2$CH$_2$CH$_2$—.

In particular embodiments of the compound, the compound is immobilized on a solid support.

The present invention further provides a compound comprising the formula

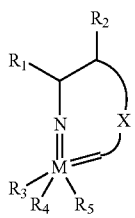

wherein M is a metal ion selected from the group consisting of Mo and W; wherein x is a carbon or carbon and heteroatom chain containing 1 to 12 carbon atoms, R$_1$ and R$_2$ can independently be selected from the group consisting of alkyl, heteroalkyl, substituted alkyl, aryl, heteroaryl, substituted aryl, cyclic, heterocyclic, substituted cyclic, and hydrogen; R$_1$ and R$_2$ can be interconnected to each other; R$_3$, R$_4$, and R$_5$ can be independently be selected from the group consisting of alkyl, heteroalkyl, substituted alkyl, aryl, heteroaryl, substituted aryl, cyclic, heterocyclic, and substituted cyclic; R$_3$, R$_4$, and R$_5$ can be interconnected to each other; and, R$_3$ and R$_4$ can be interconnected to each other and R$_5$ can be absent.

In further embodiments, n is 2; R$_1$ and R$_2$ are adjacent carbons in an aromatic ring; M is molybdenum; or any combination thereof.

In a further embodiment, the R$_3$, R$_4$, and R$_5$ are interconnected nitrogens of N,N-di (pyrrolyl-α-methyl)-N-methylamine (dpma) and each of the bonds with the M is via a separate nitrogen of the dpma.

In a further embodiment, the R$_3$ and R$_4$ are interconnected oxygens of a dialkoxide and each of the bonds with the M is via a separate oxygen of the dialkoxide.

The present invention further provides a compound comprising the formula.

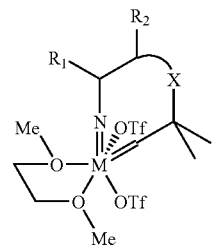

wherein M is a metal ion selected from the group consisting of Mo and W; x is an integer from 1 to 12; OTf is a triflate; R$_1$ and R$_2$ can independently be selected from the group consisting of alkyl, heteroalkyl, substituted alkyl, aryl, heteroaryl, substituted aryl, cyclic, heterocyclic, substituted cyclic, and hydrogen; and, R$_1$ and R$_2$ can be interconnected to each other.

In further embodiments, x is 2; R$_1$ and R$_2$ are adjacent carbons in an aromatic ring; M is molybdenum; or any combination thereof.

The present invention further provides a compound comprising the formula

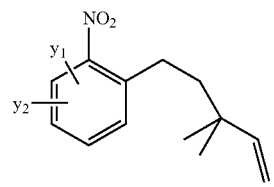

where y$_1$ and y$_2$ are each selected from alkyl containing 1 to 12 carbon atoms and hydrogen. y$_1$ or y$_2$ can be isopropyl for instance.

The present invention further provides a compound comprising the formula

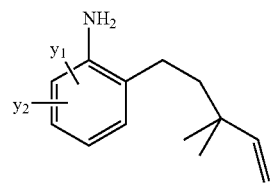

where y$_1$ and y$_2$ are each selected from alkyl containing 1 to 12 carbon atoms and hydrogen. y$_1$ or y$_2$ can be isopropyl for instance.

The present invention further provides a compound comprising MoCl$_2$(NAr)$_2$(DME) wherein Ar is aryl and dme is dimethoxyethane and the N is bound to the Mo via an imido bond.

The present invention further provides a compound comprising Mo(nph)$_2$(NAr)$_2$ wherein Ar is aryl and nph is neophylyl or neopentyl and the N is bound to the Mo via an imido bond.

The present invention further provides a compound comprising the formula

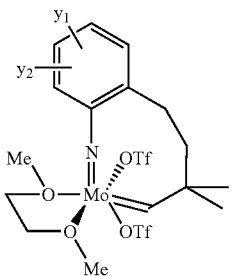

wherein OTf is a triflate and $y^1$ and $y^2$ are each selected from alkyl containing 1 to 12 carbon atoms and hydrogen. $y^1$ or $y^2$ can be isopropyl for instance.

The present invention further provides a compound comprising the formula

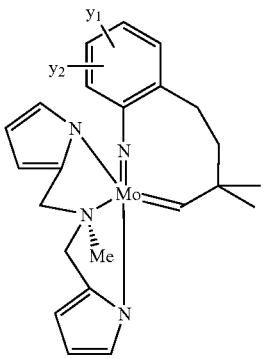

wherein $y^1$ and $y^2$ are each selected from the group consisting of alkyl containing 1 to 12 carbon atoms and hydrogen. $y^1$ or $y^2$ can be isopropyl for instance.

The present invention further provides a compound which has the structure

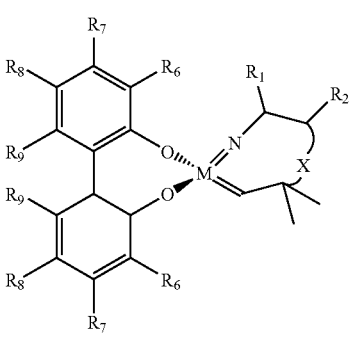

wherein M is a metal ion selected from the group consisting of Mo and W; wherein x is a carbon or carbon and heteroatom chain containing 1 to 12 carbon atoms; $R_1$ and $R_2$ can independently be selected from the group consisting of alkyl, heteroalkyl, substituted alkyl, aryl, heteroaryl, substituted aryl, cyclic, heterocyclic, substituted cyclic, and hydrogen; $R_1$ and $R_2$ can be interconnected to each other; $R_6$, $R_7$, $R^8$, and $R_9$ can be independently be selected from the group consisting of hydrogen, alkyl, heteroalkyl, substituted alkyl, aryl, heteroaryl, substituted aryl, cyclic, heterocyclic, and substituted cyclic.

The present invention further provides a process for metathesizing an olefin which comprises (a) contacting the olefin in a solvent with a metal (M) complex comprising an imido ligand (N—R) bound to the M to provide an M=N—R site, a carbon (C) bound to the M to provide an M=C reaction site, a substituted alkyl chain which tethers the C of the M=C reaction site to the R of the M=N—R site, and two to four ligands (R') bound to the M to provide two to four M-R' sites; wherein the M is selected from the group consisting of molybdenum and tungsten; the R and R' are each independently selected from the group consisting of alkyl, heteroalkyl, substituted alkyl, aryl, heteroaryl, substituted aryl, cyclic, heterocyclic, and substituted cyclic; and, the R' can be interconnected, to metathesize the olefin; and (b) separating the metathesized olefin in the solvent from the catalyst.

In a further embodiment, the R' are interconnected and each M-R' bond is between the M and an oxygen of a dialkoxide ligand or a nitrogen of an $\eta^1$-pyrrolyl ligand, particularly an $\eta^1$-pyrrolyl ligand which is N,N-di(pyrrolyl-α-methyl)-N-methylamine (dpma).

In a further embodiment, the R' is 1,2-dimethoxyethane or 3,3'-di-tert-butyl-5,5',6,6'-tetramethyl-1,1'-biphenyl-2,2'-diol.

In a further embodiment, the M is molybdenum.

In a further embodiment, the substituted alkyl chain between the C of the M=C and the R of the M=N—R comprises a backbone of 1 to 12 carbon atoms, particularly a substituted alkyl chain between the C of the M=C and the R of the M=N—R which is —C(CH_3)_2CH_2CH_2—.

In a further embodiment, the catalyst is immobilized on a solid support.

In a further embodiment, the metathesis is selected from the group consisting of ring-closing metathesis and ring-opening cyclooligomerization metathesis.

The present invention further provides a process for metathesizing an olefin which comprises (a) contacting the olefin in a solvent with a metal (M) catalyst which has the formula

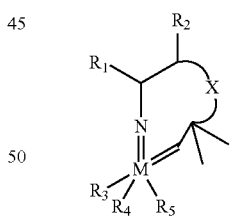

wherein x is a carbon or carbon and heteroatom (NOS) chain containing 1 to 12 carbon atoms; $R_1$ and $R_2$ can independently be selected from the group consisting of alkyl, heteroalkyl, substituted alkyl, aryl, heteroaryl, substituted aryl, cyclic, heterocyclic, substituted cyclic, and hydrogen; $R_1$ and $R_2$ can be interconnected to each other; $R_3$, $R_4$, and $R_5$ can be independently be selected from the group consisting of alkyl, heteroalkyl, substituted alkyl, aryl, heteroaryl, substituted aryl, cyclic, heterocyclic, and substituted cyclic; $R_3$, $R_4$, and $R_5$ can be interconnected to each other; and, $R_3$ and $R_4$ can be interconnected to each other and $R_5$ can be absent, to metathesize the olefin; and (b) separating the metathesized olefin in the solvent from the catalyst.

In a further embodiment, x is —C(CH$_3$)CH$_2$CH$_2$—.

In a further embodiment, R$_1$ and R$_2$ are adjacent carbons in an aromatic ring.

In a further embodiment, M is molybdenum.

In a further embodiment, the R$_3$, R$_4$, and R$_5$ are interconnected nitrogens of N,N-di(pyrrolyl-α-methyl)-N-methylamine (dpma) and each of the bonds with the M is via a separate nitrogen of the dpma.

In a further embodiment, the R$_3$ and R$_4$ are interconnected oxygens of a dialkoxide and each of the bonds with the M is via a separate oxygen of the dialkoxide.

In a further embodiment, the catalyst is immobilized on a solid support.

In a further embodiment, the metathesis is selected from the group consisting of ring-closing metathesis and ring-opening cyclooligomerization metathesis.

The present invention further provides a process for preparing a molybdenum catalyst (I) of the formula

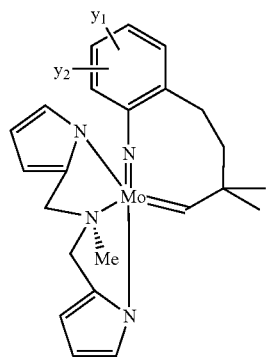

(I)

which comprises reacting a compound (II) of the formula

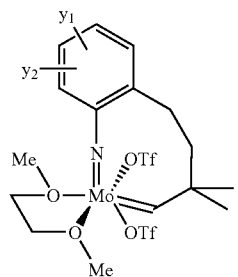

(II)

with N,N-di(pyrrolyl-α-methyl)-N-methylamine lithium salt to make the molybdenum catalyst (I), wherein y$^1$ and y$^2$ are each selected from the group consisting of lower alkyl containing 1 to 12 carbon atoms (such as isopropyl and adamantyl).

In a further process, the compound (II) is prepared by a process which comprises reacting a compound (III) of the formula

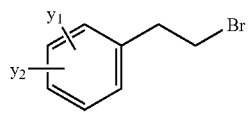

(III)

with 2-methyl-4-ZnBr-2-butene, to produce compound (IV) having the formula

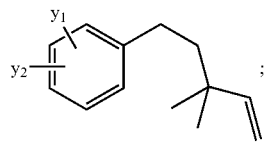

(IV)

reacting the compound (IV) with a mixture of nitric acid, acetic acid, and acetic anhydride to produce compound (V) having the formula

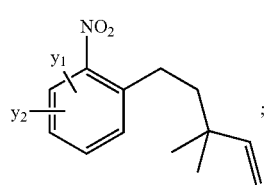

(V)

reacting compound (V) with SnCl$_2$ and an acid to produce compound (VI) having the formula

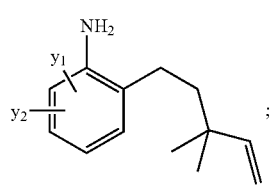

(VI)

reacting compound (VI) with dimolybdate, chlorotrimethylsilane, and triethylamine and dme to produce compound (VII) having the formula

MoCl$_2$(NAr)$_2$(dme)  (VII)

wherein Ar is aryl and dme is dimethoxyethane and the N is bound to the Mo via an imido bond; reacting compound (VII) with neophylyl (nph) MgCl to produce compound (VIII) having the formula

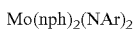

Mo(nph)$_2$(NAr)$_2$  (VIII)

wherein Ar is aryl and nph is neophylyl and the N is bound to the Mo via an imido bond; and, reacting compound (VIII) with triflic acid in DME to produce the compound (II).

The present invention relates to a process for the preparation of a Mo or W catalyst which comprises reacting a compound which comprises a metal (M) complex with an imido ligand (N—R) bound to the M to provide an M=N—R site, a carbon (C) bound to the M to provide an M=C reaction site, a substituted carbon or carbon and heteroatom (N,S,O) containing 1 to 12 carbon atoms which tethers the C of the M=C reaction site to the R of the M=N—R site, and two to four ligands (R') bound to the M to provide two to four M-R' sites; wherein the M is selected from the group consisting of molybdenum and tungsten; the R and R' are each independently selected from the group consisting of alkyl, heteroalkyl, substituted alkyl, aryl, heteroaryl, substituted aryl, cyclic, heterocyclic, and substituted cyclic; and the R' can be interconnected with an alkali metal salt of a triamine to form the catalyst.

The present invention relates to a process for the preparation of a M or W catalyst of the formula:

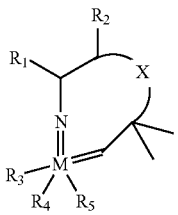

which comprises reacting a compound:

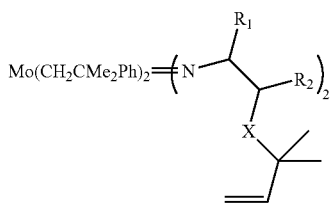

and a molar excess of triflic acid in dimethoxymethane (DME) to form the catalyst.

DETAILED DESCRIPTION OF THE INVENTION

Figure 1:
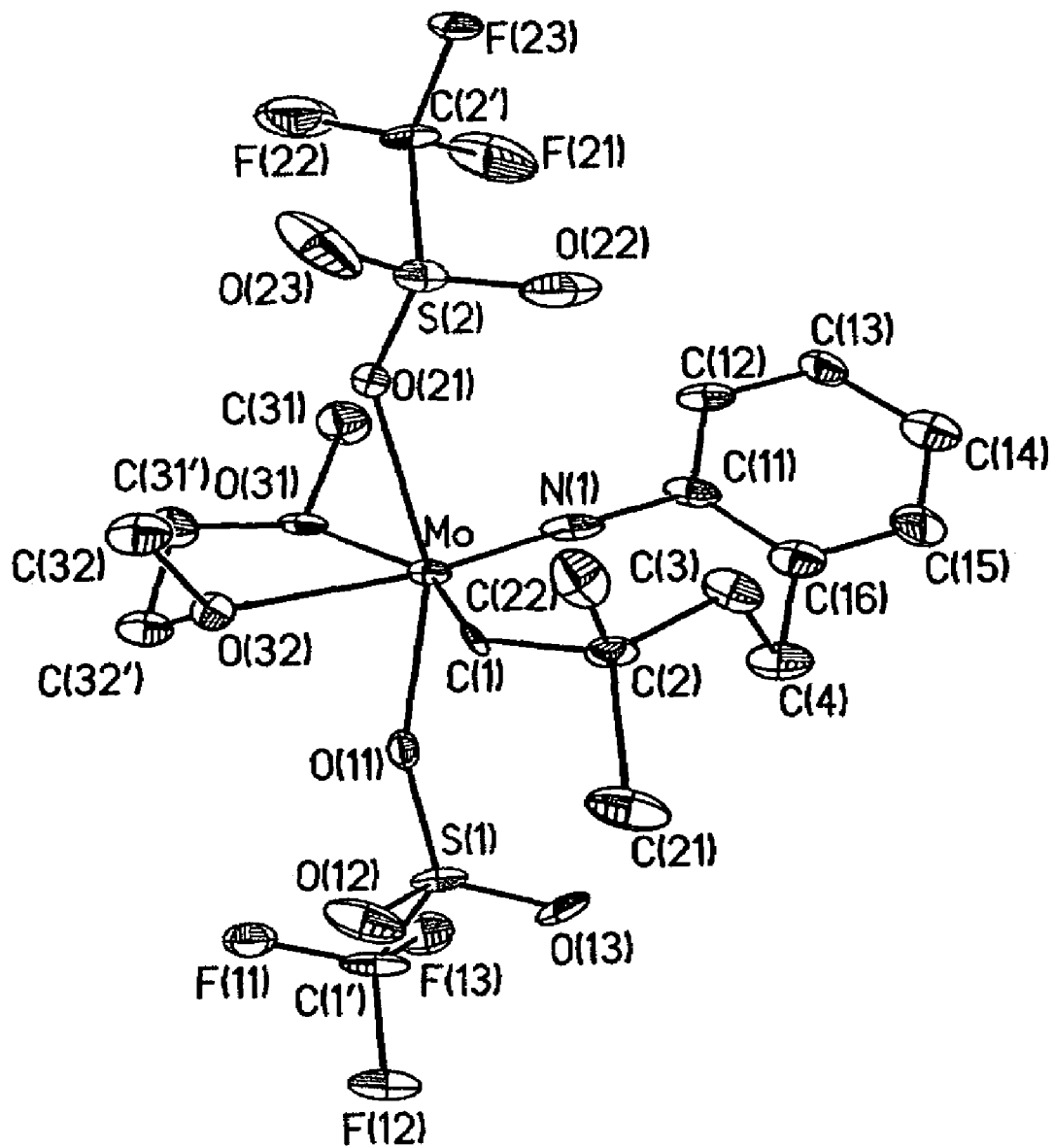
FIG. 1 is a chemical structure for x-ray diffraction.

All patents, patent applications, government publications, government regulations, and literature references cited in this specification are hereby incorporated herein by reference in their entirety. In case of conflict, the present description, including definitions, will control.

The term "olefin metathesis" refers to a reaction in which all the carbon double bonds in an olefin (alkene) are cut and then rearranged in a statistical fashion. If one of the product alkenes is volatile or easily removed, then the reaction can be driven to the right. There are a wide variety of variants of the reaction such as ring-opening metathesis polymerization and ring-closing metathesis polymerization.

The term "chiral" refers to mirror images of a molecule which are not superimposable on each other. Each mirror image is referred to as "enantiomers" and has the designation (R)-enantiomer or (S)-enantiomer. The enantiomers have a chiral center; therefore, they are stereoisomers of each other.

Current catalysts for ring-closing metathesis use ruthenium carbenes (Grubbs' catalyst) or molybdenum carbenes (Schrock's catalyst). The carbene is untethered thus, at the end of the reaction, a relatively unstable methylidene, $M=CH_2$, complex is produced which often undergoes rapid decomposition. These catalysts, when supported on a solid substrate, are not reusable. This renders the catalysts less economical for industrial applications.

In contrast to Grubbs' catalyst or Schrock's catalyst, the catalytic compound of the present invention comprises a molybdenum or tungsten metal (M) complex which comprises an imido ligand (N—R) bound to the M to provide an $M=N-R'$ site, an $M=C$ reaction site wherein the C of the $M=C$ reaction site is tethered to the R of the imido ligand via a substituted alkyl chain to form a ring structure, and two to four ligands (R') bound to the M to provide two to four M-R' sites. In particular embodiments, the M-R' sites include each of the oxygens of two alkoxides or of a dialkoxide ligand or each of the nitrogens of an $\eta^1$-pyrrolyl ligand bound to the M. Because the $M=C$ is tethered, the methylidene complex which is produced in the ring-closing reaction is trapped by the tether. This results in a more stable catalyst at the end of the ring-closing reaction which enables the catalyst to be used over and over again in ring-closing reactions. The ability to reuse the catalyst after a ring-closing reaction makes it economically viable to attach the catalysts to solid supports for industrial applications.

An illustrative example of the catalytic compound is provided comprising the formula

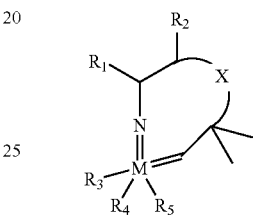

wherein M is a metal ion selected from the group consisting of Mo and W; wherein x is a carbon or a carbon and heteroatom chain containing 1 to 12 carbon atoms; $R_1$ and $R_2$ can independently be selected from the group consisting of alkyl, heteroalkyl, substituted alkyl, aryl, heteroaryl, substituted aryl, cyclic, heterocyclic, substituted cyclic, and hydrogen; $R_1$ and $R_2$ can be interconnected to each other; $R_3$, $R_4$, and $R_5$ can be independently be selected from the group consisting of alkyl, heteroalkyl, substituted alkyl, aryl, heteroaryl, substituted aryl, cyclic, heterocyclic, and substituted cyclic; $R_3$, $R_4$, and $R_5$ can be interconnected to each other; and, $R_3$ and $R_4$ can be interconnected to each other and $R_5$ can be absent.

In a further embodiment, the catalytic compound has the formula

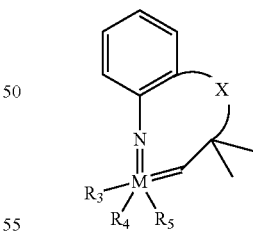

wherein M is a metal ion selected from the group consisting of Mo and W, wherein $y^1$ and $y^2$ are each selected from the group consisting of lower alkyl containing 1 to 12 carbon atoms; wherein x is a carbon or carbon and heteroatom chain containing 1 to 12 carbon atoms; $R_3$, $R_4$, and $R_5$ can be independently be selected from the group consisting of alkyl, heteroalkyl, substituted alkyl, aryl, heteroaryl, substituted aryl, cyclic, heterocyclic, and substituted cyclic; $R_3$, $R_4$, and $R_5$ can be interconnected to each other; $R_3$ and $R_4$ can be interconnected to each other and $R_5$ can be absent;

and $R_3$ and $R_4$ are separate and $R_5$ is absent. $R_3$ and $R_4$ are separate and $R_5$ is absent. This embodiment illustrates the situation where the $R_1$ and $R_2$ of the previous compound are interconnected members of an aromatic ring.

The synthesis of the novel catalytic complexes from bromoethylbenzene 1 is shown in Scheme 1. Scheme 1 shows the synthesis of a novel bis(triflate) molybdenum catalyst precursor (compound 7) and a novel $\eta^1$-pyrrolyl molybdenum catalyst (compound 8). As shown in Scheme 1, in the first step bromoethylbenzene (compound 1) is reacted with 2-methyl-4-ZnBr-2-butene in a tetrahydrofuran (THF) solution containing CuBr and bromoethylbenzene to produce (3,3-dimethyl-1-pentene)benzene (compound 2). Compound 2 is then reacted with nitric acid/acetic acid/acetic anhydride to produce 2-(3,3-dimethyl-1-pentene)-1-nitrobenzene (compound 3). The nitro group is reduced to an amino group in a reduction reaction comprising $SnCl_2$ and an acid, which produces 2-(3,3-dimethyl-1-pentene)-1-aniline (compound 4). Compound 4 is reacted with ammonium dimolybate ($NH_4Mo_2O_7$), chlorotrimethylsilane ($ClSiMe_3$), and triethylamine($NEt_3$) in dimethoxyethane (DME) to produce $MoCl_2(NAr)_2(dme)$ (compound 5) which has the structure

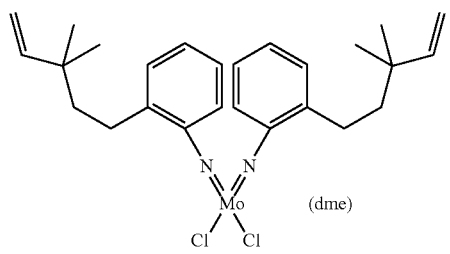

Compound 5 with neophylyl (nph) MgCl in THF to produce $Mo(nph)_2(NAr)_2$ (compound 6) which has the structure.

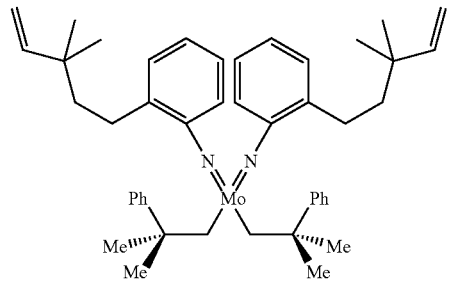

Compound 6 is then reacted with triflic acid (HO-Tf) in DME to produce the novel bis(triflate) molybdenum catalyst precursor (compound 7). The novel bis(triflate) molybdenum catalyst precursor can serve as a precursor for a plurality of catalytic complexes comprising particular ancillary ligands such as the $\eta^1$-pyrrolyl ligand of the novel $\eta^1$-pyrrolyl molybdenum catalyst (compound 8). As shown in Scheme 1, compound 7 is converted into the novel $\eta^1$-pyrrolyl molybdenum catalyst (compound 8) in a reaction comprising N,N-di(pyrrolyl-α-methyl)-N-methylamine lithium salt ($Li_2$dpma). The above reaction can also be performed wherein the metal is tungsten (W) instead of molybdenum (Mo).

Scheme 1

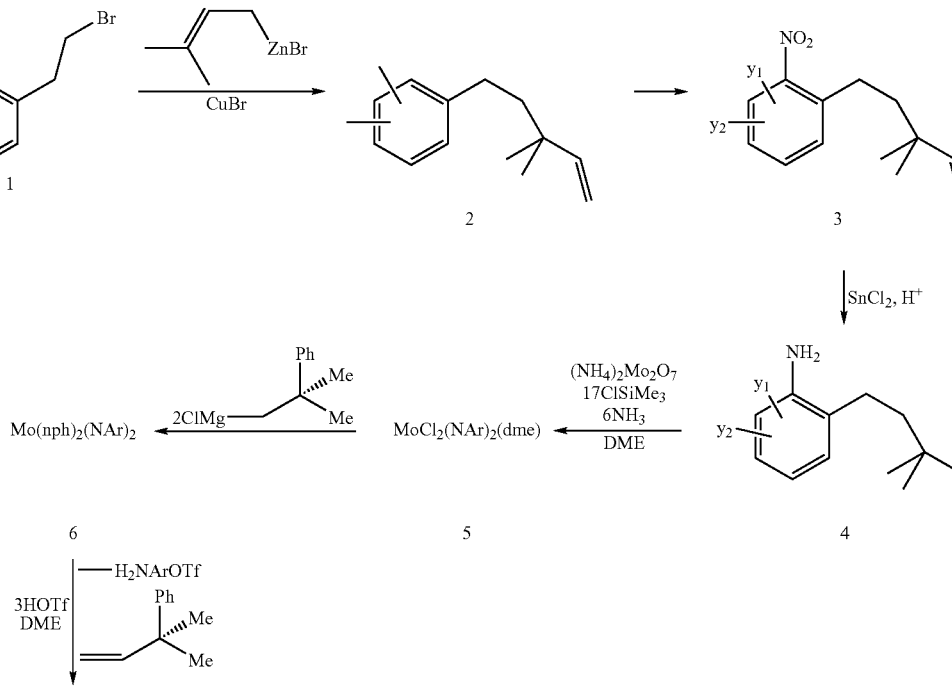

-continued

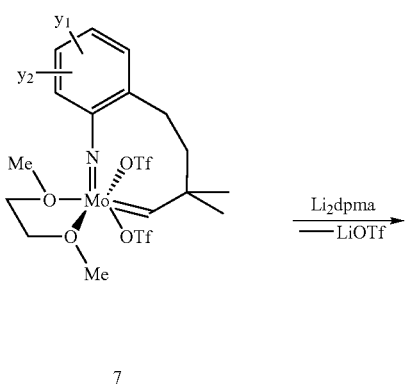

7

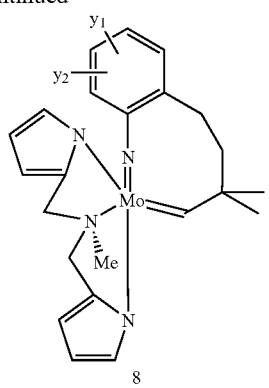

8

In particular embodiments, the ancillary ligand can be of a type which enables the catalyst to be attached to a polymer surface or it can be a chiral ancillary ligand, or both. For example, the ancillary ligand can be a dialkoxide selected from the dialkoxides disclosed in U.S. Pat. No. 6,346,652 B1 to Schrock et al. in which the oxygen atoms of the dialkoxide are bound to the Mo to form a catalytic complex with the following formula

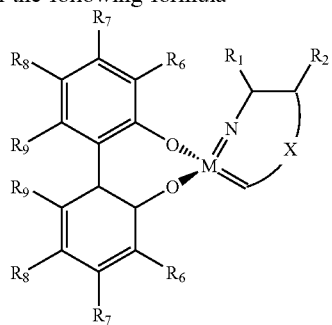

wherein M is a metal ion selected from the group consisting of Mo and W; wherein x is a carbon or carbon and heteroatom (NOS) chain containing 1 to 12 carbon atoms; $R_1$ and $R_2$ can independently be selected from the group consisting of alkyl, heteroalkyl, substituted alkyl, aryl, heteroaryl, substituted aryl, cyclic, heterocyclic, substituted cyclic, and hydrogen; $R_1$ and $R_2$ can be interconnected to each other; $R_6$, $R_7$, $R_8$, and $R_9$ can be independently be selected from the group consisting of hydrogen, alkyl, heteroalkyl, substituted alkyl, aryl, heteroaryl, substituted aryl, cyclic, heterocyclic, and substituted cyclic. Preferably, the dialkoxide is chiral which enables a catalytic olefin metathesis product to be formed that has more than 50% enantiomeric excess of at least one of the enantiomers in the mixture. The chirality of the dialkoxide above is a result of the steric interactions of the $R_9$ groups.

Hultzsch et al. in Angew. Chem. Int. Ed. 41: 589-593 (2002) discloses a method for synthesizing a molybdenum catalyst supported on a solid substrate using a dialkoxide as the ancillary ligand. The method as illustrated in Example 4 can be used to support the catalysts of the present invention on a solid substrate. Other ligands which can be used include binaphthyl ligands such as the N,N'-disubstituted-2,2'-bisamido-1,1'-binaphthyl ligand disclosed by Jamieson in Organometallics 19: 925-930 (2000). In addition to compound 7, compounds 3-6 shown above are novel as well.

The catalysts of the present invention provide new opportunities in materials and biological chemistry. The catalysts can be used to selectively polymerize cyclic olefins to form large macrocycles. Producing large macrocycles are difficult to synthesize using current methods. A scheme illustrating an example of ring-opening cyclooligomerization (ROC) is shown below in Scheme 2.

Scheme 2

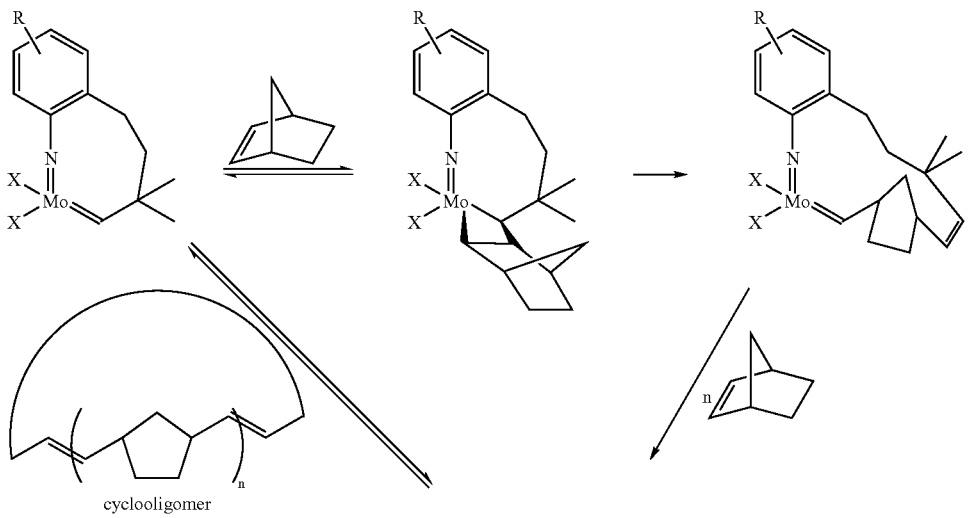

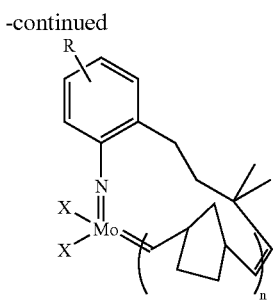

While Scheme 2 shows an example of ROC which uses norbornene as the monomer, substituted norbornylenes and a plurality of other cyclic olefins can also be used. If, for example, ester substituted norbornylenes are used, a substituted ring is formed. The ester groups can then be converted to acid chlorides using standard methods known in the art. For example, the acid chlorides can be reacted with diamines to form nylon-like linkages which then polymerizes the cyclooligomers. The character of the linkages can be altered from simple aliphatics that provide novel materials to metal complexes. Since the metal is part of the linkage, swelling of the polymer in the presence of various analytes changes the ligand field of the metal center. In other words, the color of the polymer changes on the addition of various compounds. The extent of the color change is determined by the character of the polymer which can be altered by changing the functional groups on the rings and in the linker.

Valinomycin is a member of a class of antibiotics consisting of a macrocyclic ring. Like many peptide drugs, the compounds generally suffer from a lack of bioavailability resulting from its degradation in the human body. With the cyclooligomerization catalyst disclosed herein, a plurality of unnatural ring structures with various functional groups around the periphery can be produced using combinatorial chemistry to discover particular compounds which can act as mimics for members of this antibiotic class or other classes of antibiotics. With the unparalleled case of macrocyclic ring synthesis enabled by this class of catalyst, combinatorial space for these mimics can be explored.

The following examples are intended to promote a further understanding of the present invention.

EXAMPLE 1

Details for the synthesis of 2-(3,3-dimethylpent-4-enyl) aniline (4).

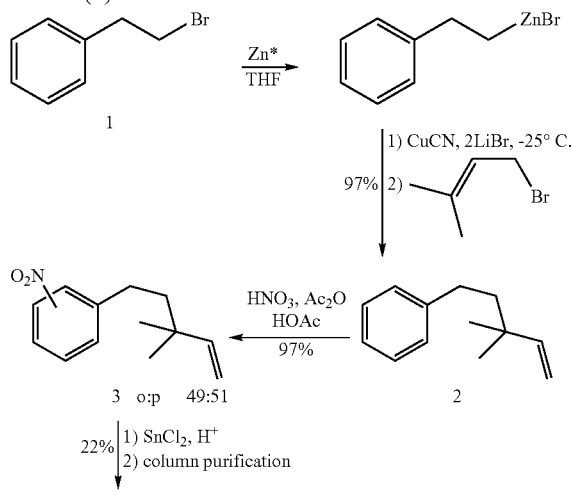

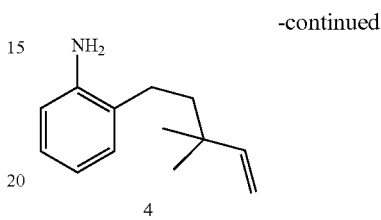

Preparation of 2-(3,3-dimethylpent-4-enyl)nitrobenzene: In a flask, was loaded fuming $HNO_3$ (18.7 mL, 90%, d=1.5), HOAc (18 mL), $Ac_2O$ (14 mL), which was allowed to cool back to room temperature before proceeding. This solution was added dropwise to 3,3-dimethyl-5-phenyl-1-pentene (45.8 g, 0.263 mol), which was prepared using the procedure of Reike and coworkers referenced as 12 in the manuscript, in $Ac_2O$ (120 mL). The reaction was kept between 0 and $-5°$ C. during the addition. After the addition, the mixture was stirred at 0° C. for 12 h. The reaction mixture was poured into crushed ice (300 g) The product was extracted with ethyl ether (3×200 mL) and the combined organic layers were washed with portions of saturated $NaHCO_3$ (~300 mL total) until no gas formed on addition of the basic aqueous solution. The organic solution was filtered, and the separated solids were washed with ether (50 mL). The combined aqueous layers were extracted with ether (3×200 mL). The combined ether solutions were dried with $MgSO_4$. The volatiles were removed in vacuo providing the product as a yellow oil in 97% yield (55.95 g) as a mixture of isomers. GC/FID analysis displayed an ortho:para ratio of 49:51. The compound was used without further purification.

Preparation of 2-(3,3-dimethylpent-4-enyl)aniline: In a 2000 mL round-bottomed three-necked flask with a thermometer and a mechanical stirrer was loaded $SnCl_2 2H_2O$ (270 g, 1.056 mol) and ethanol (500 mL). The mixture was heated to 55° C., and the crude mixture of nitroarenes prepared in the previous step (55.95 g, 0.26 mol) was added very carefully so that the temperature was kept between 65-70° C. After addition, the reaction mixture was stirred at 70° C. for 7 h. After cooling to room temperature, water (200 mL) was added. The pH of the solution was adjusted to 12 by addition of 40% NaOH. Extraction with hexane:ethyl acetate (v:v=1:1) was carried out until the extract was colorless (~5×500 mL). The combined extracts were dried with $MgSO_4$. Removing volatiles in vacuo provided 44.8 g of crude product as a red oil. GC/FID analysis show that the ratio of ortho to para products was 40:60. Column separation (silica gel, 250–400 mesh, 6:1 hexane:ethyl acetate) gave 2-(3,3-dimethylpent-4-enyl)aniline (4) in 22% yield (8.8 g). M=189.30 g/mol. $^1H$ NMR (300 MHz, $CDCl_3$): δ=7.02 (m, 2H, —$C_6H_4$—), 6.62-6.80 (m, 2H, —$C_6H_4$—), 5.78-5.96 (m, 1 H, —CH═$CH_2$), 5.03 (dd, 1 H, J=3 Hz, 5 Hz, CH═$CH_2$), 4.99 (dd, 1H, J=5 Hz, 3 Hz, —CH═$CH_2$), 3.56 (s, br, 2H, —$NH_2$), 2.31-2.46 (m, 2H, —$C_6H_4CH_2CH_2$—), 1.48-1.66 (m, 2 H, —$C_6H_4CH_2CH_2$), 1.08 (s, 6 H, —$CH_3$). $^{13}C$ NMR ($CDCl_3$): δ=147.8, 143.9, 129.2, 127.1, 126.8, 118.8, 115.4, 111.2, 41.7, 36.7, 26.6, 26.4. Elemental Analysis: Calc. For C$_{13}$H$_{19}$N: C, 82.48; H, 10.12; N, 7.40. Found: C, 82.71; H, 10.23; N, 7.56. MS (EI) m/z=189 (M$^+$). The other isomer of 4-(3,3-dimethylpent-4-enyl)aniline was isolated in 40% yield (16.0 g). $^1$H NMR (300 MHz, CDCl$_3$): δ=7.02 (dd, 2 H, J=208 Hz, 8 Hz, —C$_6$H$_4$—), 6.69 (dd, 2 H, J=6 Hz, 4 Hz, —C$_6$H$_4$—), 5.80-6.01 (m, 1 H, —CH=CH$_2$), 5.07 (m, 2 H, —CH=CH$_2$), 3.58 (s, br, 2 H, —NH$_2$), 2.42-2.58 (m, 2 H, —C$_6$H$_4$CH$_2$CH$_2$—), 1.56-1.70 (m, 2 H, —C$_6$H$_4$CH$_2$CH$_2$—), 1.13 (s, 6 H, —CH$_3$). $^{13}$C NMR (C$_6$D$_6$): δ=163.1, 148.4, 144.8, 132.9, 129.3, 115.3, 110.8, 45.6, 36.8, 30.7, 26.8. Elemental Analysis: Calc. For C$_{13}$H$_{19}$N: C, 82.48; H, 10.12; N, 7.40. Found: C, 82.43; H, 9.57; N, 7.45. MS (EI) m/z=189 (M$^+$).

Details for the synthesis of the imido-tethered carbene 7.

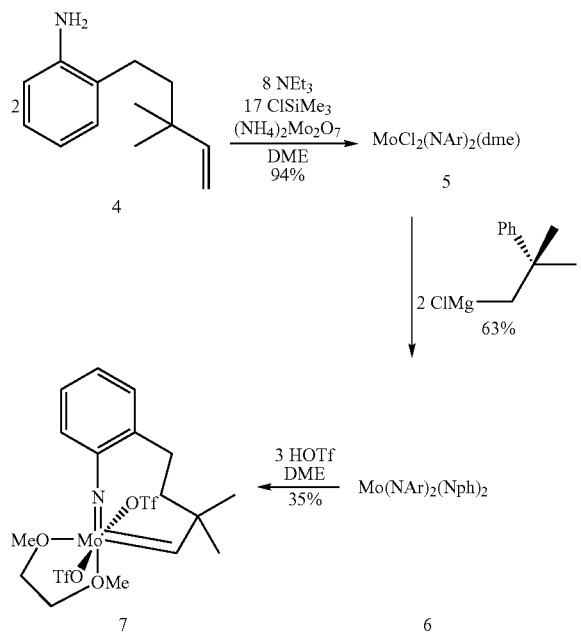

synthesis of Mo(NAr)$_2$Cl$_2$(DME) (5). In a 250 mL Schlenk flask was loaded ammonium dimolybdate (0.529 g, 2.70 mmol), 100 mL 1,2-dimethoxyethane (DME), and a stir bar. To the suspension was added triethylamine (4.37 g, 43.2 mmol), chlorotrimethylsilane (10.0 g, 92.0 mmol), and 1 (1.02 g, 5.40 mmol). The suspension was stirred at 70° C. for 12 h. After cooling to room temperature, the solution was filtered. The volatiles of the filtrate were removed in vacuo to give 1.60 g of Mo(NAr)$_2$Cl$_2$(DME) (5) as a red solid (2.53 mmol, 93.8%), which was used without further purification. $^1$H NMR (299.9 MHz, C$_6$D$_6$): δ 7.73 (d, J=7.62 Hz, 2 H), 6.94 (d, J=7.03 Hz, 2 H), 6.88 (t, J=7.62 Hz, 2 H), 6.75 (d, J=7.03 Hz, 2 H), 5.97 (m, 2 H, =CH), 5.04 (m, 4H, CH$_2$=), 3.46 (s, 4H, O—CH$_2$), 3.19 (2, 6H, O—CH$_3$), 2.85 (m, 4H), 1.72 (m, 4 H, Mo—CH$_2$), 1.15 (s, 12 H, CH$_3$). $^{13}$C NMR (75 MHz, C$_6$D$_6$): 156.14 (N—C(ipso)) 148.74, 135.84 C(ipso)-CH$_2$), 128.82, 127.23 (=CH), 126.53, 110.77 (CH$_2$=), 71.11 (O—CH$_2$), 63.02 (CMe$_2$), 44.30 (O—CH$_3$), 37.16 (ArCH$_2$), 34.51 (CMe$_2$Ph), 27.80 (ArCH$_2$CH$_2$), 26.95 (CMe$_2$).

Synthesis of Mo(NAr)$_2$Nph$_2$ (3). To a -90° C. solution of Mo(NAr)$_2$Cl$_2$(DME) (5) (4.80 g, 7.60 mmol) in 300 mL THF was added 34 mL 0.5 M solution of neophyl magnesium chloride (17 mmol, 2.2 equiv.). The solution was allowed to reach room temperature, and then stirred for 18 hours. Removal of the volatiles in vacuo left a red solid, which was dissolved in toluene and filtered to remove the magnesium chloride The volatiles were removed from the toluene solution in vacuo, leaving a red solid which was recrystallized from ether at -35° C. to give 3.50 g of 6 (4.75 mmol, 62.5%). $^1$H NMR (299.9 MHz, C$_6$D$_6$): δ 7.3 (m, 4 H), 7.1 (m, 6H), 7.0 (m, 5 H), 6.8 (m, 3H), 5.7 (m, 2 H, =CH), 4.9 (m, 4 H, =CH$_2$), 2.7 (m, 4 H), 1.90 (s, 4 H, Mo—CH$_2$), 1.6 (m, 4 H, —CH$_2$CH$_2$—), 1.46 (s, 12 H, CH$_2$CMe$_2$Ph), 1.00 (s, 12 H, imido-CH$_3$). $^{13}$C NMR (75.4 MHz, C$_6$D$_6$): δ 155.46 (N—C(ipso)), 151.16, 148.35, 135.40, 128.90, 128.62, 126.51, 126.38, 126.23, 125.62, 111.07 (=CH$_2$), 78.63 (Mo—CH$_2$), 43.58 (ArCH$_2$), 40.82 (CMe$_2$Ph), 36.93 (CMe$_2$), 32.75 (CMe$_2$Ph), 27.38 (ArCH$_2$CH$_2$), 26.94 (CMe$_2$). Anal. Calc. For C$_{46}$H$_{60}$N$_2$Mo: C, 74.97; H, 8.21; N, 3.80. Found: C, 74.93; H, 8.44; N, 3.77.

Synthesis of tethered carbene (7). A -90° C. solution of 2.05 g triflic acid (13.7 mmol, 3.0 equiv.) in DME (10 mL) was added to a -90° C. solution of Mo(NAr)$_2$(Nph)$_2$ (3) (3.32 g, 4.35 mmol) in DME (300 mL). This solution was stirred for 22 h, and then volatiles were removed in vacuo. The anilinium triflate was removed by precipitation from a minimal amount of toluene. The remaining dark solid was recrystallized from ether/pentane, giving 1.01 g of a yellow 7 (1.52 mmol, 35.0%). In fluid solution, the compound apparently exists as 3 different isomers, which made definitive assignment of many of the peaks difficult. There is dependence on temperature to the NMR spectra, and the relative amounts of each isomer changes with temperature. Schrock and coworkers have reported similar observations, including the fact that the two minor isomers are more prevalent in polar solvents However, the tethered carbene has low solubility in most solvents except THF. The spectra reported here were taken at room temperature. Assignments, where they could be definitely made, are given. $^1$H NMR (299.9 MHz, THF-d$_8$): δ 14.30, 14.27, 13.65, 8.15 (d), 7.0-7.6 (m), 3.43 (s, 4 H, OCH$_2$), 3.40 (m), 3.27 (2, 6 H, OCH$_3$) 2.47 (m), 2.31 (s), 1.08 (m). $^{13}$C NMR (75.4 MHz, THF-d$_8$): δ 333.83, 330.83, 326.96, 155.64, 154.83, 154.62, 149.77, 149.44, 148.55, 138.43, 130.801, 130.39, 129.67, 129,42, 129.21, 129.21, 129.11, 128.91, 128.29, 127.42, 126.90, 126.80, 126.29, 126.03, 122.39, 118.18, 72.75, 66.30, 59.92, 59.59, 59.52, 58.90, 45.98, 45.85, 45.00, 30.16, 29.74, 29.30, 28.51, 27.85, 21.48, 15.68. $^{19}$F (282.2 MHz, THF-d$_8$): -78.45, -78.58, -79.56, -79.64. Anal. Calc. For C$_{18}$H$_{25}$F$_6$MoNO$_8$S$_2$; C, 32.98; H, 3.83; N, 2.13. Found: C, 33.43; H, 4.07; N, 2.12.

Bis(Triflate) 7 exhibits low solubility in many common solvents. However, crystals sufficient for a preliminary x-ray diffraction study were obtained. The results are shown in Tables 1, 2 and 3 hereinafter.

TABLE 1

| Crystal data and structure refinement for 7 | |
|---|---|
| Identification code | jtcx2 |
| Empirical formula | C18 H25 F6 Mo N O8 S2 |
| Formula weight | 657.45 |
| Temperature | 176(2) K |
| Wavelength | 0.71073 A |
| Crystal system, space group | Monoclinic, P2(1)/n |
| Unit cell dimensions | a = 12.669(3) A Alpha = 90 deg. |
| | b = 15.745(5) A Beta = 92.648(6) deg. |
| | c = 12.809(4) A Gamma = 90 deg. |
| Volume | 2552.3(12) A^3 |
| Z, Calculated density | 4, 1.711 Mg/m^3 |
| Absorption coefficient | 0.764 mm^-1 |
| F(000) | 1328 |

TABLE 1-continued

Crystal data and structure refinement for 7

| | |
|---|---|
| Crystal size | 0.14 × 0.19 × 0.37 mm |
| Theta range for data collection | 2.05 to 23.37 deg. |
| Limiting indices | −14 <= h <= 13, −15 <= k <= 17, −14 <= l <= 10 |
| Reflections collected/unique | 11563/3698 [R(int) = 0.2814] |
| Completeness to theta = 23.37 | 99.4% |
| Absorption correction | sadabs |
| Refinement method | Full-matrix least-squares on $F^2$ |
| Data/restraints/parameters | 3698/0/326 |
| Goodness-of-fit on $F^2$ | 0.971 |
| Final R indices [I > 2sigma(I)] | R1 = 0.1088, wR2 = 0.2494 |
| R indices (all data) | R1 = 0.2107, wR2 = 0.3341 |
| Extinction coefficient | 0.0000(5) |
| Largest diff. Peak and hole | 1.528 and −2.874 e.$\text{Å}^{-3}$ |

TABLE 2

Atomic coordinates (×10^4) and equivalent isotropic displacement parameters ($\text{Å}^2 \times 10^3$) for tethered. U(eq) is defined as one third of the trace of the orthogonalized

| | x | y | z | U(eq) |
|---|---|---|---|---|
| Mo | 9078(1) | 4616(1) | 7718(1) | 28(1) |
| S(1) | 11522(4) | 4720(4) | 7048(4) | 42(2) |
| S(2) | 6498(4) | 4296(4) | 7546(4) | 44(2) |
| O(11) | 10686(9) | 5022(8) | 7765(8) | 31(3) |
| O(12) | 11292(11) | 4959(12) | 5980(9) | 70(5) |
| O(13) | 11958(10) | 3947(10) | 7289(11) | 60(4) |
| O(21) | 7450(8) | 4831(8) | 7855(8) | 31(3) |
| O(22) | 6689(11) | 3384(14) | 7530(13) | 85(6) |
| O(23) | 5899(13) | 4679(14) | 6697(13) | 106(8) |
| O(31) | 9096(8) | 5791(9) | 8898(8) | 35(3) |
| O(32) | 8904(8) | 5847(8) | 6778(8) | 35(3) |
| N(1) | 9135(10) | 3794(12) | 8607(9) | 41(5) |
| F(11) | 12246(8) | 6256(9) | 7405(9) | 56(3) |
| F(12) | 13377(9) | 5329(9) | 6920(9) | 71(4) |
| F(13) | 12847(8) | 5318(8) | 8492(9) | 60(4) |
| F(21) | 6201(12) | 4185(13) | 9520(11) | 109(6) |
| F(22) | 5493(12) | 5289(13) | 8763(15) | 118(7) |
| F(23) | 4805(8) | 4052(8) | 8518(11) | 73(4) |
| C(1) | 9111(13) | 4039(12) | 6483(13) | 35(5) |
| C(1') | 12563(15) | 5423(18) | 7495(14) | 54(7) |
| C(2) | 9069(14) | 3057(13) | 6042(14) | 39(5) |
| C(2') | 5707(17) | 4508(19) | 8650(20) | 64(7) |
| C(3) | 9007(14) | 2429(14) | 6923(14) | 44(5) |
| C(4) | 9998(15) | 2346(17) | 7719(14) | 58(7) |
| C(11) | 9142(14) | 3077(15) | 9222(13) | 39(6) |
| C(12) | 8681(13) | 3081(15) | 10174(13) | 40(6) |
| C(13) | 8712(15) | 2346(15) | 10756(14) | 44(5) |
| C(14) | 9224(14) | 1597(16) | 10449(14) | 49(6) |
| C(15) | 9656(15) | 1605(15) | 9456(15) | 50(6) |
| C(16) | 9618(14) | 2345(16) | 8814(14) | 46(6) |
| C(21) | 10067(16) | 2954(17) | 5411(14) | 69(8) |
| C(22) | 8103(17) | 2998(14) | 5265(14) | 54(6) |
| C(31') | 8847(15) | 6558(14) | 8405(13) | 42(5) |
| C(31) | 8589(17) | 5660(15) | 9878(14) | 55(6) |
| C(32') | 9289(13) | 6545(14) | 7362(13) | 39(5) |
| C(32) | 7943(14) | 6024(15) | 6149(13) | 50(6) |

TABLE 3

Bond length [Å] and angles [deg] for tethered.

| | |
|---|---|
| Mo—N(1) | 1.723(16) |
| Mo—C(1) | 1.827(19) |
| Mo—O(21) | 2.105(11) |
| Mo—O(11) | 2.133(11) |
| Mo—O(32) | 2.287(12) |
| Mo—O(31) | 2.389(13) |
| S(1)—O(13) | 1.366(15) |
| S(1)—O(12) | 1.435(13) |
| S(1)—O(11) | 1.511(12) |
| S(1)—C(1') | 1.79(2) |
| S(2)—O(23) | 1.431(15) |
| S(2)—O(22) | 1.46(2) |
| S(2)—O(21) | 1.509(12) |
| S(2)—C(2') | 1.80(2) |
| O(31)—C(31') | 1.39(2) |
| O(31)—C(31) | 1.45(2) |
| O(32)—C(32') | 1.40(2) |
| O(32)—C(32) | 1.456(19) |
| N(1)—C(11) | 1.38(2) |
| F(11)—C(1') | 1.38(3) |
| F(12)—C(1') | 1.30(2) |
| F(13)—C(1') | 1.32(2) |
| F(21)—C(2') | 1.36(3) |
| F(22)—C(2') | 1.27(3) |
| F(23)—C(2') | 1.35(3) |
| C(1)—C(2) | 1.65(3) |
| C(2)—C(3) | 1.51(3) |
| C(2)—C(22) | 1.54(3) |
| C(2)—C(21) | 1.54(2) |
| C(3)—C(4) | 1.59(2) |
| C(4)—C(16) | 1.50(2) |
| C(11)—C(12) | 1.38(2) |
| C(11)—C(16) | 1.41(3) |
| C(12)—C(13) | 1.38(3) |
| C(13)—C(14) | 1.41(3) |
| C(14)—C(15) | 1.41(3) |
| C(15)—C(16) | 1.43(3) |
| C(31')—C(32') | 1.47(2) |
| N(1)—Mo—C(1) | 101.4(7) |
| N(1)—Mo—O(21) | 94.4(5) |
| C(1)—Mo—O(21) | 102.3(6) |
| N(1)—Mo—O(11) | 101.3(5) |
| C(1)—Mo—O(11) | 96.5(6) |
| O(21)—Mo—O(11) | 152.5(5) |
| N(1)—Mo—O(32) | 169.9(6) |
| C(1)—Mo—O(32) | 88.3(6) |
| O(21)—Mo—O(32) | 80.6(4) |
| O(11)—Mo—O(32) | 80.2(4) |
| N(1)—Mo—O(31) | 99.5(6) |
| C(1)—Mo—O(31) | 159.0(6) |
| O(21)—Mo—O(31) | 78.7(4) |
| O(11)—Mo—O(31) | 76.6(4) |
| O(32)—Mo—O(31) | 71.0(4) |
| O(13)—S(1)—O(12) | 120.8(10) |
| O(13)—S(1)—O(11) | 115.5(8) |
| O(12)—S(1)—O(11) | 112.3(8) |
| O(13)—S(1)—C(1') | 101.1(11) |
| O(12)—S(1)—C(1') | 104.9(10) |
| O(11)—S(1)—C(1') | 97.9(8) |
| O(23)—S(2)—O(22) | 119.2(12) |
| O(23)—S(2)—O(21) | 110.7(9) |
| O(22)—S(2)—O(21) | 115.0(8) |
| O(23)—S(2)—C(2') | 102.9(13) |
| O(22)—S(2)—C(2') | 107.0(12) |
| O(21)—S(2)—C(2') | 99.1(10) |
| S(1)—O(11)—Mo | 125.7(7) |
| S(2)—O(21)—Mo | 131.5(8) |
| C(31')—O(31)—C(31) | 114.5(15) |
| C(31')—O(31)—Mo | 112.9(10) |
| C(31)—O(31)—Mo | 116.5(12) |
| C(32')—O(32)—C(32) | 113.9(15) |
| C(32')—O(32)—Mo | 111.1(10) |
| C(32)—O(32)—Mo | 120.8(11) |
| C(11)—N(1)—Mo | 173.3(14) |
| C(2)—C(1)—Mo | 139.7(12) |
| F(12)—C(1')—F(13) | 110.2(18) |
| F(12)—C(1')—F(11) | 107.2(19) |
| F(13)—C(1')—F(11) | 105.3(17) |
| F(12)—C(1')—S(1) | 109.8(15) |
| F(13)—C(1')—S(1) | 113.3(16) |
| F(11)—C(1')—S(1) | 110.7(14) |

TABLE 3-continued

Bond length [A] and angles [deg] for tethered.

| | |
|---|---|
| C(3)—C(2)—C(22) | 112.1(16) |
| C(3)—C(2)—C(21) | 113.3(18) |
| C(22)—C(2)—C(21) | 107.6(15) |
| C(3)—C(2)—C(1) | 111.2(14) |
| C(22)—C(2)—C(1) | 106.9(15) |
| C(21)—C(2)—C(1) | 105.3(16) |
| F(22)—C(2')—F(21) | 111(2) |
| F(22)—C(2')—F(23) | 110.1(19) |
| F(21)—C(2')—F(23) | 105.(2) |
| F(22)—C(2')—S(2) | 113.7(19) |
| F(21)—C(2')—S(2) | 109.0(16) |
| F(23)—C(2')—S(2) | 107.7(18) |
| C(2)—C(3)—C(4) | 118.0(16) |
| C(16)—C(4)—C(3) | 108.7(15) |
| N(1)—C(11)—C(12) | 121(2) |
| N(1)—C(11)—C(16) | 116.7(16) |
| C(12)—C(11)—C(16) | 123(2) |
| C(11)—C(12)—C(13) | 118(2) |
| C(12)—C(13)—C(14) | 123.6(19) |
| C(13)—C(14)—C(15) | 117(2) |
| C(14)—C(15)—C(16) | 122(2) |
| C(11)—C(16)—C(15) | 117.2(19) |
| C(11)—C(16)—C(4) | 120.4(19) |
| C(15)—C(16)—C(4) | 122(2) |
| O(31)—C(31')—C(32') | 108.2(17) |
| O(32)—C(32')—C(31') | 110.9(16) |

Symmetry transformations used to generate equivalent atoms:

TABLE 5

Hydrogen coordinates ($\times 10^4$) and isotropic displacement parameters ($A^2 \times 10^3$) for tethered.

| | x | y | z | U(eq) |
|---|---|---|---|---|
| H(1A) | 9171 | 4418 | 5932 | 42 |
| H(3A) | 8869 | 1874 | 6619 | 53 |
| H(3B) | 8400 | 2577 | 7321 | 53 |
| H(4A) | 10375 | 1823 | 7588 | 69 |
| H(4B) | 10477 | 2818 | 7628 | 69 |
| H(12B) | 8357 | 3568 | 10417 | 49 |
| H(13B) | 8378 | 2344 | 11387 | 53 |
| H(14A) | 9274 | 1122 | 10880 | 59 |
| H(15A) | 9975 | 1116 | 9213 | 60 |
| H(21A) | 10090 | 2389 | 5131 | 103 |
| H(21B) | 10683 | 3051 | 5860 | 103 |
| H(21C) | 10051 | 3358 | 4849 | 103 |
| H(22B) | 8044 | 2430 | 4997 | 82 |
| H(22C) | 8190 | 3387 | 4698 | 82 |
| H(22D) | 7474 | 3140 | 5617 | 82 |
| H(31A) | 9145 | 7028 | 8811 | 51 |
| H(31B) | 8087 | 6630 | 8341 | 51 |
| H(31C) | 8643 | 6170 | 10290 | 82 |
| H(31D) | 8931 | 5202 | 10255 | 82 |
| H(31E) | 7858 | 5523 | 9739 | 82 |
| H(32A) | 9101 | 7067 | 6995 | 47 |
| H(32B) | 10053 | 6515 | 7434 | 47 |
| H(32C) | 8009 | 6563 | 5808 | 75 |
| H(32D) | 7352 | 6039 | 6592 | 75 |
| H(32E) | 7834 | 5587 | 5633 | 75 |

TABLE 4

Anisotropic displacement parameters ($A^2 \times 10^3$) for tethered. The anisotropic displacement factor exponent takes the form:
$-2\pi^2[h^2 a^{*2} U11 + \ldots + 2 h k a^* b^* U12]$

| | U11 | U22 | U33 | U23 | U13 | U12 |
|---|---|---|---|---|---|---|
| Mo | 16(1) | 44(1) | 26(1) | 2(1) | 5(1) | −1(1) |
| S(1) | 20(2) | 70(5) | 39(3) | 08(3) | 15(2) | 3(3) |
| S(2) | 22(3) | 58(4) | 53(3) | −2(3) | 8(2) | −7(2) |
| O(11) | 34(7) | 21(7) | 37(7) | 3(5) | 1(5) | −1(6) |
| O(12) | 53(10) | 134(16) | 25(8) | −1(8) | 7(7) | −37(9) |
| O(13) | 26(8) | 64(12) | 91(11) | −6(9) | 24(7) | 19(8) |
| O(21) | 25(7) | 31(9) | 37(7) | 2(5) | 6(5) | −2(5) |
| O(22) | 31(9) | 116(19) | 110(14) | −26(12) | 29(8) | −13(10) |
| O(23) | 62(11) | 160(20) | 91(13) | 71(13) | 050(10) | −78(12) |
| O(31) | 15(6) | 67(11) | 24(7) | 8(6) | 8(5) | −3(6) |
| O(32) | 19(6) | 53(10) | 34(7) | 15(6) | −10(5) | 1(6) |
| N(1) | 20(8) | 98(16) | 5(7) | −1(8) | 6(6) | 4(8) |
| F(11) | 38(7) | 53(10) | 79(9) | −11(7) | 26(6) | −6(6) |
| F(12) | 35(7) | 114(13) | 65(8) | −18(7) | 27(6) | −19(7) |
| F(13) | 33(6) | 84(11) | 62(8) | −8(7) | −3(5) | 1(6) |
| F(21) | 73(10) | 190(20) | 63(10) | 20(10) | 20(8) | −43(11) |
| F(22) | 71(11) | 97(16) | 195(19) | −36(13) | 83(11) | −15(10) |
| F(23) | 19(6) | 54(10) | 147(12) | 3(8) | 26(7) | −10(6) |
| C(1) | 30(10) | 29(13) | 47(12) | 30(9) | 15(8) | 2(9) |
| C(1') | 28(11) | 110(20) | 29(12) | −22(12) | 18(9) | −17(13) |
| C(2) | 34(11) | 50(15) | 35(11) | −9(9) | 22(9) | −1(9) |
| C(2') | 28(13) | 80(20) | 86(19) | 8(16) | 39(12) | 7(13) |
| C(3) | 39(12) | 69(17) | 24(10) | 2(10) | 1(9) | −17(11) |
| C(4) | 26(11) | 90(20) | 54(14) | −4(12) | 4(10) | −9(11) |
| C(11) | 24(10) | 79(18) | 14(10) | 16(10) | 3(8) | −7(10) |
| C(12) | 21(10) | 78(18) | 23(10) | −3(10) | 6(8) | −3(10) |
| C(13) | 38(12) | 61(17) | 36(12) | 13(11) | 12(9) | −8(11) |
| C(14) | 25(11) | 90(20) | 34(12) | 6(11) | −16(9) | 017(11) |
| C(15) | 37(12) | 60(17) | 55(14) | −11(12) | 2(10) | −21(11) |
| C(16) | 23(11) | 78(19) | 37(12) | 13(12) | −6(9) | −5(11) |
| C(21) | 54(15) | 120(20) | 35(13) | −15(12) | 19(11) | −32(14) |
| C(22) | 77(16) | 53(17) | 34(12) | −7(10) | 13(11) | 14(12) |
| C(31') | 38(12) | 62(17) | 27(11) | 11(10) | 2(9) | −3(11) |
| C(31) | 55(14) | 75(19) | 35(12) | 2(10) | 13(10) | 2(12) |
| C(32') | 21(10) | 63(16) | 32(11) | −13(10) | −3(8) | 13(10) |
| C(32) | 25(11) | 90(20) | 32(11) | −3(11) | −9(9) | −4(11) |

The isomer observed is line drawn in Scheme 2, and a structural representation from the diffraction study is shown in FIG. 1. When the structure of 7 is compared to that reported for Mo(OTf)$_2$(N-2,6-DiPr$^1$C$_6$H$_3$)(neopentylidene)(DME)(Schrock, R. R., et al., *J. Am. Chem. Soc.* 112 3875 (1990)), no ring strain is apparent in the metallocycle as judged by comparison of bond distances and angles.

As would be expected, the tethered carbene 7 is an active catalyst for the ROMP of norbornylene. The materials generated in those polymerizations are currently under scrutiny. Various substitution reactions on the triflate groups are being investigated as a means of synthesizing more functional metathesis catalysts.

EXAMPLE 2

This example illustrates the synthesis of a supported catalyst comprising the catalyst of the present invention. The process produces a bidentate phenol supported on styrene and then in a two-step reaction replaces the dialkoxide of compound 7 with the bidentate biphenol supported on styrene. The process follows the synthetic pathway described in Hultzsch et al. in Angew. Chem. Int. Ed. 41: 589-593 (2002) for supporting chiral molybdenum-based catalysts on styrene.

The process is illustrated in scheme 3.

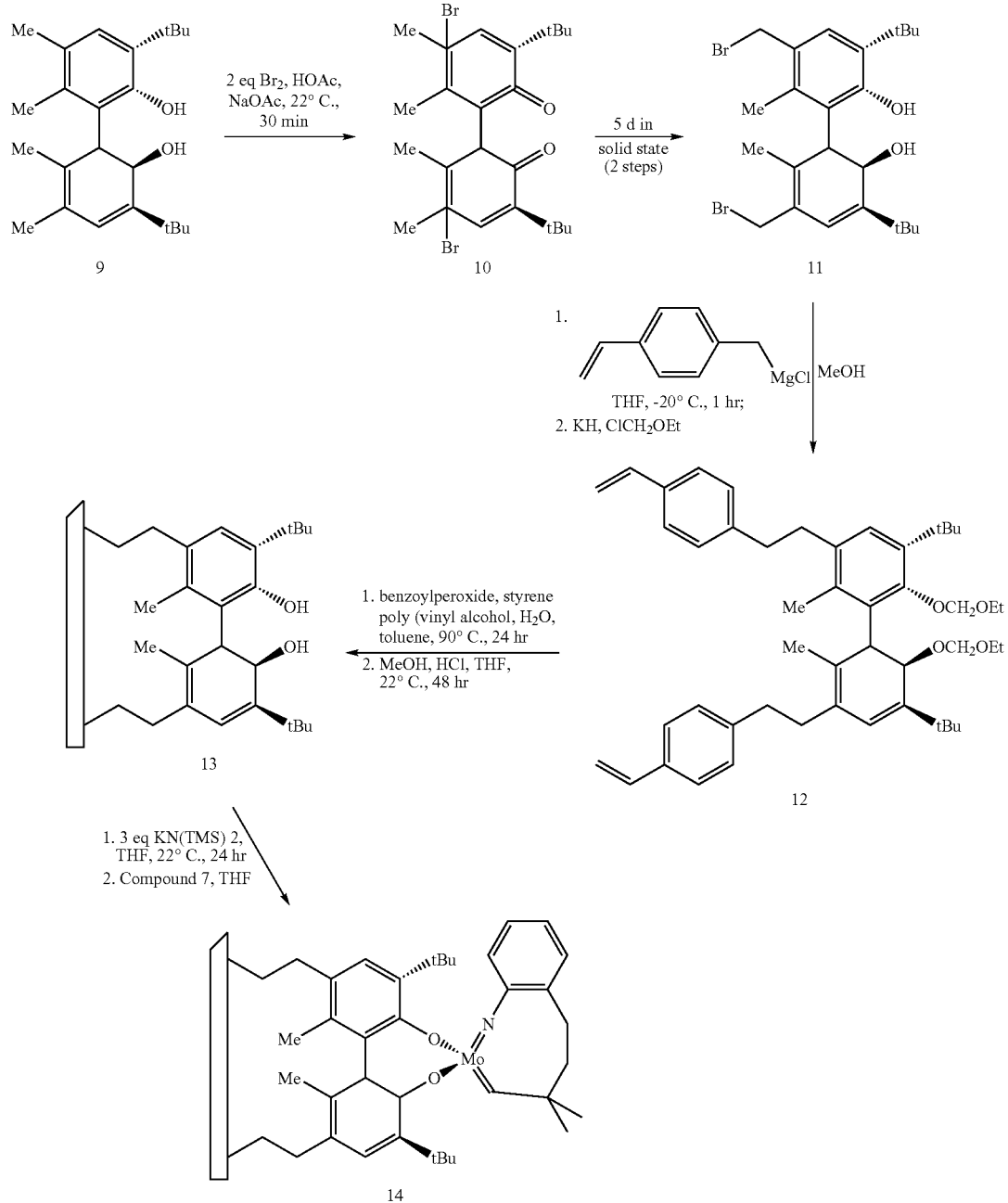

Using the process described in Alexander et al. in J. Am. Chem. Soc. 120: 4041-4042 (1998), 3,4-dimethylphenol is alkylated in a closed reaction. The 3,4-dimethylphenol is placed in a container containing 1.5 g $H_2SO_4$ and purged with isobutylene. The mixture is then place under an isobutylene atmosphere at about 20 psi (1.40614 $kgf/cm^2$) and then heated at about 70° C. until the liquid ceases to expand (about 3 hours). The reaction is then cooled, $EtO_2$ is added, and the mixture is washed with $NaHCO_3$ (3×150 mL). The combined organic layers are then dried over $MgSO_4$ and volatile solvents removed in vacuo leaving behind an oil. The alkylated product is subjected to biaryl coupling conditions consisting incubating in $K_2CrO_7$, $H_2SO_4$, $H_2O$, glacial acetic acid at 60° C. for an hour to produce the biphenol, 3,3'-di-tert-butyl-5,5',6,6'-tetramethyl-1,1'-biphenyl-2,2'-diol (9). Resolution of the biphenol leads to its chiral forms.

(R)-3,3'-di-tert-butyl-5,6,5',6'-tetramethyl-biphenyl-2,2'-diol ligand (18.1 g, 51.1 mmol) (9) and sodium acetate (16.9 g 206 mmol) are suspended in glacial acetic acid (450 mL). A solution of bromine (17.9 g, 112 mmol) in glacial acetic acid (40 mL) is then added to the suspension over a 30 minute time period in a dropwise fashion. As the solution is being added to the suspension, the ligand gradually dissolves. After the ligand has dissolved, the resulting yellow-orange solution is stirred for 15 minutes, after which ice-water (1000 mL) is added to the solution to form a precipitate. The suspension is stirred for 15 minutes and then filtered. The precipitate (pale yellow solid) is captured by the filter and washed with water (5×100 mL). The solid is then collected and dissolved in $Et_2O$ (500 mL). The organic layer is then separated from the residual water and dried over anhydrous $MgSO_4$. Removal of the solvent in vacuo gives a ring-brominated cyclohexadienone (25.1 g) as a pale yellow solid, which is stored in a sealed flask for five days. During this period the solid turns brown and then off-white. The resulting off-white solid is recrystallized from hexane at 0° C. to give compound 10 as an off-white powder in two crops (22.4 g, 86%).

A solution of p-vinylbenzyl magnesium chloride is prepared from freshly distilled p-vinylbenzyl chloride (6.56 g, 43.0 mmol) and magnesium powder (4.18 g, 172 mmol) in ether (80 mL), filtered, and cooled to about 0° C. A cold solution of 10 above (5.12 g, 10.0 mmol) in THF (40 mL) is added dropwise to the solution. Afterwards, the resulting mixture is warmed to 22° C. and stirred for 90 minutes. Then the reaction is quenched by sequential addition of methanol (20 mL) and saturated aqueous $NH_4Cl$ (40 mL). The aqueous layer is washed with $Et_2O$ (2×40 mL) and the combined organic layers are dried over anhydrous $MgSO_4$ and in vacuo. Silica gel chromatography with pentane gives the desired alkylation product (3,3'-di-tert-butyl-6,6'-dimethyl-5,5'-bis-[2-(4-vinyl-phenyl)-ethyl]-biphenyl-2,2'-diol) (11) as a white solid (3.01 g, 51%; Rf=0.05). (oligomeric side-products are not eluted under these conditions.)

A solution of the styryl functionalized biphenol (3,3'-Di-tert-butyl-6,6'-dimethyl-5,5'-bis-[2-(4-vinyl-phenyl)-ethyl]-biphenyl-2,2'-diol) (1.93 g, 3.29 mmol) (11) in THF (40 mL) is treated with small portions of solid KH (500 mg, 12.5 mmol). The suspension is allowed to stir for 5 hours, then cooled to −20° C. and treated with chloromethyl ethyl ether (1.25 g, 13.2 mmol). The mixture is then stirred for 2 hours at 22° C. Afterwards, the mixture is then cooled −20° C. and stirred for an additional hour. Solvent is removed in vacuo and the remaining solid is washed with pentane (3×20 mL). The combined pentane washes are filtered to remove KCl. Evaporation of solvents in vacuo affords compound 12 as a pale yellow oil (2.20 g, 95%). The product is of sufficient purity for subsequent polymerization, but may be further purified by column chromatography with pentane/EtOAc (50:1).

A suspension of the above compound 12 (412 mg, 0.0586 mmol), styrene (4.20 g, 40.3 mmol), divinylbenzene (83 mg, 55% of 0.64 mmol), benzoyl peroxide (48 mg, 0.14 mmol, containing 30% water), poly(vinyl alcohol) (46 mg), toluene (6 mL) and water (50 mL) are combined and stirred vigorously at 22° C. for an hour to homogenize the particle size. The suspension is then heated at about 90° C. for 24 hours. The polymer is then washed thoroughly with THF, methanol, and pentane and then dried in vacuo for 24 hours. The resulting bis(methoxy ethoxy ether) is suspended in 30 mL of concentrated HCl, methanol, and THF (1:10:50) for 48 hours. Afterwards, the polymer is isolated by filtration, washed thoroughly with THF, methanol, and pentane and then dried in vacuo for 24 hours at about 60° C. to give compound 13 as white beads.

Solid potassium hexamethyldisilazane ($KN(TMS)_2$) (94 mg, 0.47 mmol) is added to a suspension of the above compound 13 in THF (10 mL). After agitating for 24 hours, the polymer is filtered and washed with THE (3×5 mL). The polymer is then dried in vacuo and resuspended in 8 mL of THE. To this is added 108 mmol of compound 7 and the suspension agitated for 7 hours to produce compound 14. Compound 14 is washed with THF (4×5 mL) and pentane (2×5 mL) and then dried in vacuo.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A compound which comprises:
   a metal (M) complex with an imido ligand (N—R) bound to the N to provide an M=N—R site, a carbon (C) bound to the N to provide an M=C reaction site, a substituted carbon or carbon and heteroatom (N,S,O) containing 1 to 12 carbon atoms which tethers the C of the M=C reaction site to the R of the M=N—R site, and two to four ligands (R') bound to the M to provide two to four M-R' sites;
   wherein the N is selected from the group consisting of molybdenum and tungsten; the R and R' are each independently selected from the group consisting of alkyl, heteroalkyl, substituted alkyl, aryl, heteroaryl, substituted aryl, cyclic, heterocyclic, and substituted cyclic; and, the R' can be interconnected.

2. The compound of claim 1 wherein the R' are interconnected and each M-R' bond is between the M and an oxygen of a dialkoxide ligand or a nitrogen of an $\eta^1$-pyrrolyl ligand.

3. The compound of claim 2 wherein the $\eta^1$-pyrrolyl ligand is N,N-di(pyrrolyl-α-methyl)-N-methylamine (dpma).

4. The compound of claim 1 wherein the R' is 1,2dimethoxyethane or 3,3'-di-tertbutyl-5,5',6,6'-tetramethyl-1,1'-biphenyl-2,2'-diol.

5. The compound of claim 1 wherein the M is molybdenum.

6. The compound of claim 1 wherein the substituted alkyl chain between the C of the M=C and the R of the M=N—R comprises a backbone of 1 to 12 carbon atoms.

7. The compound of claim 1 wherein the substituted alkyl chain between the C of the M=C and the R of the M=N—R is —$C(CH_3)_2CH_2CH_2$—.

8. The compound of claim 1 wherein the compound is immobilized on a solid support.

9. A compound of the formula

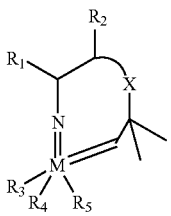

wherein M is a metal ion selected from the group consisting of Mo and W; wherein x is a carbon or carbon and heteroatom chain containing 1 to 12 carbon atoms; $R_1$ and $R_2$ can independently be selected from the group consisting of alkyl, heteroalkyl, substituted alkyl, aryl, heteroaryl, substituted aryl, cyclic, heterocyclic, substituted cyclic, and hydrogen; $R_1$ and $R_2$ can be interconnected to each other; $R_3$, $R_4$, and $R_5$ can be independently be selected from the group consisting of alkyl, heteroalkyl, substituted alkyl, aryl, heteroaryl, substituted aryl, cyclic, heterocyclic, and substituted cyclic; $R_3$, $R_4$, and $R_5$ can be interconnected to each other; $R_3$ and $R_4$ can be interconnected to each other and $R_5$ can be absent; and $R_3$ and $R_4$ are separate and $R_5$ is absent.

10. The compound of claim 9 wherein n is 2.

11. The compound of claim 9 wherein $R_1$ and $R_2$ are adjacent carbons in an aromatic ring.

12. The compound of claim 9 wherein M is molybdenum.

13. The compound of claim 9 wherein the $R_3$, $R_4$, and $R_5$ are interconnected nitrogens of N,N-di(pyrrolyl-α-methyl)-N-methylamine (dpma) and each of the bonds with the M is via a separate nitrogen of the dpma.

14. The compound of claim 9 wherein the $R_3$ and $R_4$ are interconnected oxygens of a dialkoxide and each of the bonds with the M is via a separate oxygen of the dialkoxide.

15. A compound of the formula

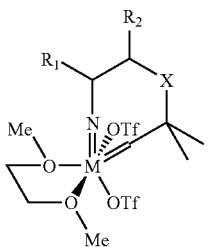

wherein M is a metal ion selected from the group consisting of Mo and W; x is a carbon or carbon and heteroatom (N,O,S) containing 1 to 12 carbon atoms; OTf is a triflate; $R_1$ and $R_2$ can independently be selected from the group consisting of alkyl, heteroalkyl, substituted alkyl, aryl, heteroaryl, substituted aryl, cyclic, heterocyclic, substituted cyclic, and hydrogen; and, $R_1$ and $R_2$ can be interconnected to each other.

16. The compound of claim 15 wherein x is —C(CH$_3$)$_2$CH$_2$CH$_2$—.

17. The compound of claim 15 wherein $R_1$ and $R_2$ are adjacent carbons in an aromatic ring.

18. The compound of claim 15 wherein M is molybdenum.

19. A compound of the formula

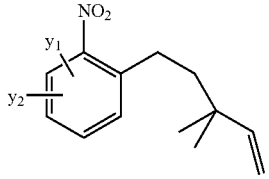

wherein $y_1$ and $y_2$ are each selected from the group consisting of hydrogen and lower alkyl containing 1 to 12 carbon atoms.

20. A compound of the formula

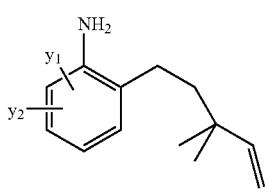

wherein $y_1$ and $y_2$ are each selected from the group consisting of hydrogen and lower alkyl containing 1 to 12 carbon atoms.

21. A compound of the formula MoCl$_2$(NAr)$_2$(dme) wherein ArN is 2-(3,3dimethyl-1-pentene)-1-phenyl-N= and dme is dimethoxymethane and the N is bound to the Mo via an imido bond.

22. A compound of the formula Mo(nph)$_2$(NAr)$_2$ wherein ArN is 2-(3,3-dimethyl-1-pentene)-1-phenyl-N= and nph is neophylyl or neopentyl and the N is bound to the Mo via an imido bond.

23. A compound of the formula

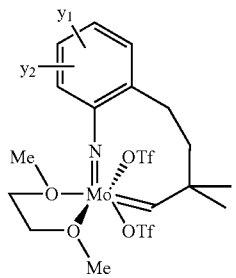

wherein OTf is a triflate, and wherein $y_1$ and $y_2$ are each selected from the group consisting of hydrogen and lower alkyl containing 1 to 12 carbon atoms.

24. A compound of the formula

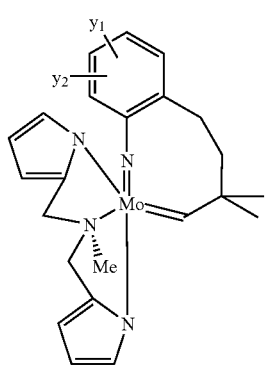

wherein $y_1$ and $y_2$ are each selected from the group consisting of hydrogen and lower alkyl containing 1 to 12 carbon atoms.

25. A compound which has the structure

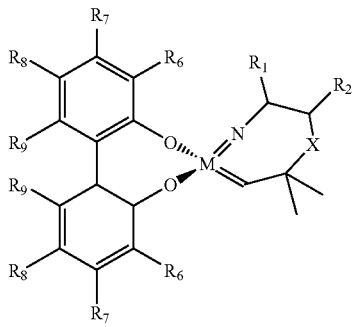

wherein M is a metal ion selected from the group consisting of Mo and W; x is a carbon group or a carbon and heteroatom (NOS) chain containing 1 to 12 carbon atoms; $R_1$ and $R_2$ can independently be selected from the group consisting of alkyl, heteroalkyl, substituted alkyl, aryl, heteroaryl, substituted aryl, cyclic, heterocyclic, substituted cyclic, and hydrogen; $R_1$ and $R_2$ can be interconnected to each other; $R_6$, $R_7$, $R_8$, and $R_9$ can be independently be selected from the group consisting of hydrogen, alkyl, heteroalkyl, substituted alkyl, aryl, heteroaryl, substituted aryl, cyclic, heterocyclic, and substituted cyclic.

26. A process for metathesizing an olefin which comprises:

(a) contacting the olefin in a solvent with a metal (M) complex comprising an imido ligand (N—R) bound to the M to provide an M=N—R site, a carbon (C) bound to the M to provide an M=C reaction site, a substituted carbon or carbon and heteroatom (N,S,O) containing 1 to 12 carbon atoms which tethers the C of the M=C reaction site to the R of the M=N—R site, and two to four ligands (R') bound to the M to provide two to four M-R' sites;

wherein the M is selected from the group consisting of molybdenum and tungsten; the R and R' are each independently selected from the group consisting of alkyl, heteroalkyl, substituted alkyl, aryl, heteroaryl, substituted aryl, cyclic, heterocyclic, and substituted cyclic; and, the R' can be interconnected, to metathesize the olefin; and (b) separating the metathesized olefin in the solvent from the catalyst.

27. The process of claim 26 wherein the R' are interconnected and each M-R' bond is between the M and an oxygen of a dialkoxide ligand or a nitrogen of an $\eta^1$-pyrrolyl ligand.

28. The process of claim 27 wherein the $\eta^1$-pyrrolyl ligand is N,N-di(pyrrolyl-α-methyl)-N-methylamine (dpma).

29. The process of claim 26 wherein the R' is 1,2-dimethoxyethane or 3,3'-di-tert-butyl-5,5',6,6'-tetramethyl-1,1'-biphenyl-2,2'-diol.

30. The process of claim 26 wherein the M is molybdenum.

31. The process of claim 26 wherein the chain between the C of the M=C and the R of the M=N—R comprises an alkylene backbone of 1 to 8 carbon atoms.

32. The process of claim 26 wherein the chain between the C of the M=C and the R of the M=N—R is —C(CH$_3$)$_2$CH$_2$CH$_2$—.

33. The process of claim 26 wherein the catalyst is immobilized on a solid support.

34. The process of claim 26 wherein the metathesis is selected from the group consisting of ring-closing metathesis and ring-opening cyclooligomerization metathesis.

35. A process for metathesizing an olefin which comprises:

(a) contacting the olefin in a solvent with a metal (M) catalyst which has the formula

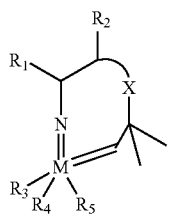

wherein x is a carbon or carbon and heteroatom chain containing 1 to 12 carbon atoms; $R_1$ and $R_2$ can independently be selected from the group consisting of alkyl, heteroalkyl, substituted alkyl, aryl, heteroaryl, substituted aryl, cyclic, heterocyclic, substituted cyclic, and hydrogen; $R_1$ and $R_2$ can be interconnected to each other; $R_3$, $R_4$, and $R_5$ can be independently be selected from the group consisting of alkyl, heteroalkyl, substituted alkyl, aryl, heteroaryl, substituted aryl, cyclic, heterocyclic, and substituted cyclic; $R_3$, $R_4$, and $R_5$ can be interconnected to each other; $R_3$ and $R_4$ can be interconnected to each other and $R_5$ can be absent, and $R_3$ and $R_4$ can be separate from each other and $R_5$ is missing, to metathesize the olefin; and (b) separating the metathesized olefin in the solvent from the catalyst.

36. The process of claim 35 wherein n is 2.

37. The process of claim 35 wherein $R_1$ and $R_2$ are adjacent carbons in an aromatic ring.

38. The process of claim 35 wherein M is molybdenum.

39. The process of claim 35 wherein the $R_3$, $R_4$, and $R_5$ are interconnected nitrogens of N,N-di(pyrrolyl-α-methyl)-N-methylamine (dpma) and each of the bonds with the M is via a separate nitrogen of the dpma.

40. The process of claim 35 wherein the $R_3$ and $R_4$ are interconnected oxygens of a dialkoxide and each of the bonds with the M is via a separate oxygen of the dialkoxide.

41. The process of claim 35 wherein the catalyst is immobilized on a solid support.

42. The process of claim 35 wherein the metathesis is selected from the group consisting of ring-closing metathesis and ring-opening cyclooligomerization metathesis.

43. A process for preparing a molybdenum catalyst (I) of the formula

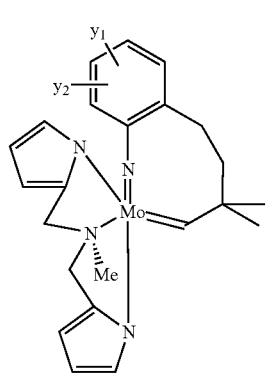

wherein $y_1$ and $y_2$ are each selected from the group consisting of hydrogen and lower alkyl containing 1 to 12 carbon atoms, which comprises:

reacting a compound (II) of the formula

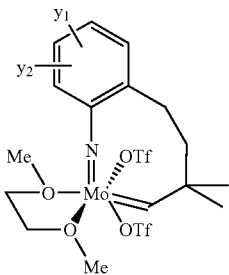

(II)

with N,N-di(pyrrolyl-α-methyl)-N-methylamine lithium salt to make the molybdenum catalyst (I).

44. The process of claim 43 wherein compound (II) is prepared by a process which comprises reacting a compound (III) of the formula

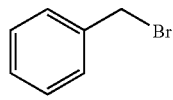

(III)

with 2-methyl-4-ZnBr-2-butene, to produce compound (IV) having the formula

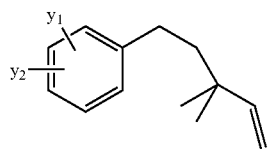

(IV)

reacting the compound (IV) with nitric acid/acetic acid/acetic anhydride to produce compound (V) having the formula

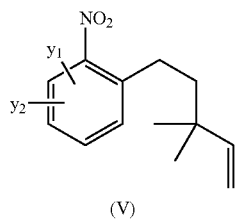

(V)

reacting compound (V) with $SnCl_2$ and an acid to produce compound (VI) having the formula

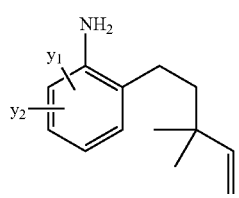

(VI)

reacting compound (VI) with dimolybdate, chlorotrimethylsilane, and triethylamine to produce compound (VII) having the formula $$MoCl_2(NAr)_2(dme) \qquad (VII)$$

wherein Ar is aryl and dime is dimethoxymethane and the N is bound to the Mo via an imido bond;

reacting compound (VII) with neophylyl (nph) MgCl to produce compound (VIII) having the formula $$Mo(nph)_2(NAr)_2 \qquad (VIII)$$

wherein Ar is aryl and nph is neophylyl and the N is bound to the Mo via an imido bond; and, reacting compound (VIII) with triflic acid in DME to produce the compound (II).

45. A process for the preparation of a Mo or W catalyst which comprises reacting a compound which comprises: a metal (M) complex with an imido ligand (N—R) bound to the M to provide an M=N—R site, a carbon (C) bound to the N to provide an M=C reaction site, a substituted carbon or carbon and heteroatom (N,S,O) containing 1 to 12 carbon atoms which tethers the C of the M=C reaction site to the R of the M=N—R site, and two to four ligands (R') bound to the M to provide two to four M-R' sites;

wherein the M is selected from the group consisting of molybdenum and tungsten; the R and R' are each independently selected from the group consisting of alkyl, heteroalkyl, substituted alkyl, aryl, heteroaryl, substituted aryl, cyclic, heterocyclic, and substituted cyclic; and the R' can be interconnected.

46. A process for the preparation of a M or W catalyst of the formula:

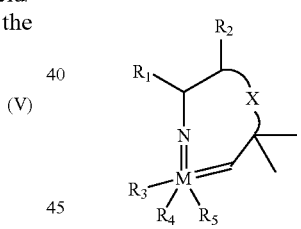

which comprises reacting a compound

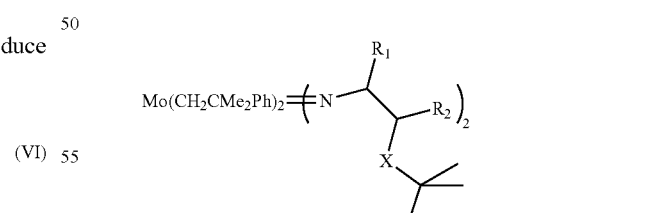

and a molar excess of triflic acid and dimethoxymethane (DME) to form the catalyst.

* * * * *

UNITED STATES PATENT AND TRADEMARK OFFICE
CERTIFICATE OF CORRECTION

PATENT NO.         : 7,250,523 B2                                   Page 1 of 1
APPLICATION NO. : 10/691328
DATED              : July 31, 2007
INVENTOR(S)        : Aaron L. Odom and James T. Ciszewski It is certified that error appears in the above-identified patent and that said Letters Patent is hereby corrected as shown below:

Column 10, line 1, "M=N–R' site" should be --M=N–R site--.

Column 17, line 54, "6.75 (d," should be --6.75 (t,--.

Column 26, lines 19 and 21, "THE" should be --THF--.

Column 26, lines 36 and 37, "to the N to provide" should be --to the M to provide--.

Column 26, line 43, "N is selected" should be --M is selected--.

Column 32, line 7, "and dime is dimethoxymethane" should be --and dme is dimethoxymethane--.

Signed and Sealed this

Twenty-seventh Day of May, 2008

JON W. DUDAS
*Director of the United States Patent and Trademark Office*